(12) United States Patent
Lin et al.

(10) Patent No.: US 9,289,128 B2
(45) Date of Patent: Mar. 22, 2016

(54) IN VIVO FLOW CYTOMETRY BASED ON CELLULAR AUTOFLUORESCENCE

(71) Applicant: The General Hospital Corporation, Boston, MA (US)

(72) Inventors: Charles P. Lin, Arlington, MA (US); Alicia L. Carlson, Medford, MA (US); Clemens Alt, Watertown, MA (US); David P. Biss, Brighton, MA (US); Costas M. Pitsillides, Larnaca (CY); Chungiang Li, Belmont, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 14/041,047

(22) Filed: Sep. 30, 2013

(65) Prior Publication Data
US 2014/0031647 A1    Jan. 30, 2014

Related U.S. Application Data

(62) Division of application No. 12/867,141, filed as application No. PCT/US2009/038567 on Mar. 27, 2009, now Pat. No. 8,574,859.

(60) Provisional application No. 61/039,891, filed on Mar. 27, 2008.

(51) Int. Cl.
*G01N 33/537* (2006.01)
*A61B 5/00* (2006.01)
(Continued)

(52) U.S. Cl.
CPC ............. *A61B 5/0071* (2013.01); *A61B 5/0059* (2013.01); *G01N 33/537* (2013.01);
(Continued)

(58) Field of Classification Search
CPC .. A61B 5/0071; A61B 5/0059; G01N 33/537; Y10T 436/13
See application file for complete search history.

(56) References Cited

U.S. PATENT DOCUMENTS 5,072,382 A   12/1991   Kamentsky
5,127,730 A   7/1992   Brelje et al.
(Continued)

FOREIGN PATENT DOCUMENTS

WO   9834536   8/1998

OTHER PUBLICATIONS

Zharov et al. In vivo Photoacoustic Flow Cytometry for Monitoring of Circulating Single Cancer Cells and Contrast Agents, Optics Letters. 31 (24): 3623-3625 (Dec. 15, 2006).*
(Continued)

*Primary Examiner* — Gail R Gabel
(74) *Attorney, Agent, or Firm* — Nutter McClennen & Fish LLP; Konstantin M. Linnik; Isaac A. Hubner

(57) ABSTRACT

The present invention generally provides methods and systems for performing in vivo flow cytometry by using blood vessels as flow chambers through which flowing cells can be monitored in a live subject in vivo without the need for withdrawing a blood sample. In some embodiments, one or more blood vessels are illuminated with radiation so as to cause a multi-photon excitation of an exogenous fluorophore that was previously introduced into the subject to label one or more cell types of interest. In some other embodiments, rather than utilizing an exogenous fluorophore, endogenous (intrinsic) cellular fluorescence can be employed for in vivo flow cytometry. The emission of fluorescence radiation from such fluorophores in response to the excitation can be detected and analyzed to obtain information regarding a cell type of interest.

19 Claims, 11 Drawing Sheets

(51) Int. Cl.
*G01N 33/569* (2006.01)
*G01N 15/14* (2006.01)
*G01N 15/00* (2006.01)

(52) U.S. Cl.
CPC ...... *G01N33/56972* (2013.01); *G01N 15/1434* (2013.01); *G01N 2015/008* (2013.01); *G01N 2015/1497* (2013.01); *Y10T 436/13* (2015.01)

(56) References Cited

U.S. PATENT DOCUMENTS

| | | |
|---|---|---|
| 5,270,171 A | 12/1993 | Cercek et al. |
| 5,434,081 A | 7/1995 | Maekawa |
| 5,644,388 A | 7/1997 | Maekawa et al. |
| 5,976,502 A | 11/1999 | Khoobehi et al. |
| 6,337,920 B1 | 1/2002 | Muhlhoff et al. |
| 6,462,345 B1 | 10/2002 | Simon et al. |
| 6,507,400 B1 | 1/2003 | Pina et al. |
| 6,548,796 B1 | 4/2003 | Silvermintz et al. |
| 6,549,275 B1 | 4/2003 | Cabuz et al. |
| 6,554,775 B1 | 4/2003 | Peyman et al. |
| 6,589,792 B1 | 7/2003 | Malachowski |
| 6,597,438 B1 | 7/2003 | Cabuz et al. |
| 6,646,742 B1 | 11/2003 | Gangstead et al. |
| 6,687,052 B1 | 2/2004 | Wilson et al. |
| 6,727,071 B1 | 4/2004 | Dunlay et al. |
| 6,743,634 B2 | 6/2004 | Kramer |
| 6,811,983 B2 | 11/2004 | Sugden et al. |
| 7,264,794 B2 | 9/2007 | Georgakoudi et al. |
| 7,491,502 B2 * | 2/2009 | Lin .............. 435/7.21 |
| 7,745,155 B2 * | 6/2010 | Lin et al. ......... 435/7.23 |
| 8,165,663 B2 | 4/2012 | Hyde et al. |
| 8,178,342 B2 | 5/2012 | Lin |
| 8,211,660 B2 * | 7/2012 | Lin et al. ......... 435/7.23 |
| 8,285,367 B2 * | 10/2012 | Hyde et al. ............ 600/476 |
| 8,574,859 B2 | 11/2013 | Lin et al. |
| 2005/0101524 A1 | 5/2005 | Hogg |
| 2006/0134002 A1 | 6/2006 | Lin |
| 2006/0134005 A1 | 6/2006 | Lin et al. |
| 2007/0111225 A1 | 5/2007 | Lambert et al. |
| 2007/0249734 A1 | 10/2007 | Gilbert et al. |
| 2007/0274919 A1 | 11/2007 | Dertinger |
| 2007/0299327 A1 | 12/2007 | Georgakoudi et al. |
| 2010/0049041 A1 | 2/2010 | Lin |
| 2011/0004910 A1 | 1/2011 | Eyer |
| 2011/0060232 A1 * | 3/2011 | Lin et al. ............ 600/504 |

OTHER PUBLICATIONS

Zhong et al. Multiphoton in vivo flow cytometry. Lasers and Electro-Optics (2005).*
Petrovsky et al. Near-Infrared Fluorescent Imaging of Tumor Apoptosis, Cancer Research 63: 1936-1942 (Apr. 15, 2003).*
Novak et al. In vivo flow cytometer for real-time detection and quantification of circulating cells, Optical Letters, 29 (1): 77-79 (Jan. 1, 2004).*
Georgakoudi et al. In Vivo Flow Cytometer: A New Method for Enumerating Circulating Cancer cells, Cancer Research, 64: 5044-5047 (Aug. 1, 2004).*
Sokolov K, Drezek R, Gossage K, Richards-Kortum R. Reflectance spectroscopy with polarized light: is it sensitive to cellular and nuclear morphology? Opt Express 1999; 5: 302-17.
Solovey, A., et al., "Sickle cell vascular endothelial growth factor on circulating and unanchored endothelial cells", 1999, Blood 93(11):3824-3830.
Spradling A, Drummond-Barbosa D, Kai T. Stem cells find their niche. Nature 2001; 414: 98-104.
Streekstra G, Hoekstra A, Nijhof E-J, Heethaar R. Light scattering by red blood cells in ektacytometry:Fraunhofer versus anomalous diffraction. Appl Opt 1993; 32: 2266-72.
Stroun, M., et al., "The origin and mechanism of circulating DNA", 2000, Ann N Y Acad Sci 906:161-168.
Sulowska, Z., et al., "Effect of exogenous opioid peptides on TNF-alpha-induced human neutrophil apoptosis in vitro", 2003, Archivum Immunologiae et Therapiae Experimentalis 51(4):267-272.
Sweeney TJ, Mailander V, Tucker AA, et al. Visualizing the kinetics of tumor-cell clearance in living animals. Proc Natl Acad Sci U S A 1999; 96: 12044-9.
Terstappen L, de Grooth B, ten Napel C, van Berkel W, Greve J. Discrimination of human cytotoxic lymphocytes from regulatory and B-lymphocytes by orthogonal light scattering. J Immunol Methods 1986; 95: 211-6.
Terstappen L, deGrooth B, Visscher K, van Kouterik F, Greve J. Four-parameter white blood cell differential counting based on light scattering measurements. Cytometry 1988; 9: 39-43.
Thompson, C.B., "Apoptosis in the pathogenesis and treatment of disease", 1995, Science 267(5203):1456-1462.
Uckun FM, Manivel C, Arthur D, et al. In vivo efficacy of B43 (anti-CD19)-pokeweed antiviral protein immunotoxin against human pre-B cell acute lymphoblastic leukemia in mice with severe combined immunodeficiency. Blood 1992; 79: 2201-14.
Uckun, F.M., et al., "Effective immunochemotherapy of CALLA+C mu+ human pre-B acute lymphoblastic leukemia in mice with severe combined immunodeficiency using B43 (anti-CD19)-pokeweed antiviral protein immunotoxin plus cylophosphamide", 1992a, Blood 79(12):3116-3129.
Venditti A, Buccisano F, Del Poeta G, et al. Level of minimal residual disease after consolidation therapy predicts outcome in acute myeloid leukemia. Blood 2000; 96: 3948-52.
Wang JH, Doyle M, Manning BJ, et al. Cutting edge: bacterial lipoprotein induces endotoxin-independent tolerance to septic shock. J Immunol 2003; 170: 14-8.
Wang W, Wyckoff JB, Frohlich VC, et al. Single cell behavior in metastatic primary mammary tumors correlated with gene expression patterns revealed by molecular profiling. Cancer Res 2002; 62: 6278-88.
Weber, W.A., et al., "Tumor angiogensis targeting using imaging agents", 2001, Quarterly Journal of Nuclear Medicine 45(2):179-182.
Wulf G, Luo K, Goodell M, Brenner M. Anti-CD45-mediated cytoreduction to facilitate allogeneic stem cell tranplantation. Blood 2003; 101: 2434-39.
Yamamoto et al., Granulocytes from patients with paroxysmal nocturnal hemoglobinuria and normal individuals have the same sensitivity to spontaneous apoptosis, Experimental Hematology 30: 187-194 (2002).
Hoffman R, Benz E, Shattil S, et al Hematology: Basic Principles and Practice. New York: Churchill Livingstone, 2000. 2 pages.
Holdenrieder, S., "Apoptotic markers in cancer", 2004, Clin Biochem 37(7):605-617.
Huberty C Applied Discriminant Analysis. New York: Wiley, 1994. 2 pages.
Janossy G, Bollum FJ, Bradstock KF, Ashley J. Cellular phenotypes of normal and leukemic hemopoietic cells determined by analysis with selected antibody combinations. Blood 1980; 56: 430-41.
Jarh, S., "DNA fragments in the blood plasma of cancer patients: quantitations and evidence for their origin from apoptotic and necrotic cells", 2001, Cancer Res 61(4):1659-1665.
Johnston, J.B., et al., "Induction of apoptosis in CD4+ prolymphocytic leukemia by deoxyadenosine and 2'-deoxycoformycin", 1992, Leukemia Research 16(8):781-788.
Kaihara S, Borenstein J, Koka R ea. Silicon micromachining to tissue engineer branched vascular channels for liver fabrication. Tissue Eng 2000; 6: 105-17.
Kiger AA, White-Cooper H, Fuller MT. Somatic support cells restrict germline stem cell self-renewal and promote differentiation. Nature 2000; 407: 750-4.
Knechtli CJ, Goulden NJ, Hancock JP, et al. Minimal residual disease status before allogeneic bone marrow transplantation is an important determinant of successful outcome for children and adolescents with acute lymphoblastic leukemia. Blood 1998;92: 4072-9.
Konrad M, Metzler M, Panzer S, et al. Late relapses evolve from slow-responding subclones in t(12;21)-positive acute lymphoblastic leukemia: evidence for the persistence of a preleukemic clone. Blood 2003; 101: 3635-40.

(56) References Cited

OTHER PUBLICATIONS

Krauter J, Wattjes MP, Nagel S, et al. Real-time RT-PCR for the detection and quantification of AML1/MTG8 fusion transcripts in t(8;21)-positive AML patients. Br J Haematol 1999; 107: 80-5.

Laxman, B., "Noninvasive real-time imaging of apoptosis", 2002, Proceedings of the National Academy of Sciences of the United States of America 99(26):16551-16555.

Lein M, Koenig F, Misdraji J, et al. Laser-induced hyperthermia in rat prostate cancera; role of site of tumor implantation. Urology 2000; 56: 167-72.

Massoud, T.F., et al., "Molecular imaging in living subjects: seeing fundamental biological processes in a new light", 2003, Genes & Development, 17(5):545-580.

Matsubara, K., et al., "Induction of apoptosis in childhood acute leukemia by chemotherapeutic agents: failure to detect evidence of apoptosis in vivo", 1994, European Journal of Haematology 52(1):47-52.

Michelson A et al., Evaluation of platelet function by flow Cytometry. Methods vol. 21, 259-270, 2000.

Momma T, Hamblin MR, Wu HC, Hasan T. Photodynamic therapy of orthotopic prostate cancer with benzoporphyrin derivative: local control and distant metastasis. Cancer Res 1998; 58: 5425-31.

Mourant JR, Bigio I, Boyer J, Conn R, Johnson TM, Shimada T. Spectroscopic diagnosis of bladder cancer with elastic scattering spectroscopy. Lasers Surg Med 1995; 17: 350-7.

Mourant JR, Bigio I, Boyer J, Johnson TM, Lacey J. Elastic scattering spectroscopy as a diagnostic for differentiating pathologies in the gastrointestinal tract: preliminary testing. J Biomed Opt 1996; 1: 192-9.

Mourant JR, Canpolat M, Brocker C, et al. Light scattering from cells: the contribution of the nucleus and the effects of proliferative status. J Biomed Opt 2000; 5: 131-7.

Mourant JR, Freyer JP, Hielscher AH, Eick AA, Shen D, Johnson TM. Mechanisms of light scattering from biological cells relevant to noninvasive optical-tissue diagnostics. Appl Opt 1998; 37: 3586-93.

Mourant JR, Johnson TM, Carpenter S, Guerra A, Aida T, Freyer JP. Polarized angular dependent spectroscopy of epithelial cells and epithelial cell nuclei to determine the size scale of scattering structures. J Biomed Opt 2002; 7: 378-87.

Muller MG, Valdez T, Georgakoudi I, et al. Spectroscopic detection and evaluation of morphologic and biochemical changes in early human oral carcinoma. Cancer 2003; 97: 1681-92.

Muller MG, Wax A, Georgakoudi I, Dasari R, Feld MS. A reflectance spectrofluorimeter for real-time spectral diagnosis of disease. Rev Sci Instrum 2002; 73: 3933-7.

Myakov A, Nieman L, Wicky L. Utzinger U, Richards-Kortum R, Sokolov K. Fiber optic probe for polarized reflectance spectroscopy in vivo: Design and performance. J Biomed Opt 2002; 7: 388-97.

Nathan D, Orkin S, Ginsburg D, Look A Hematology of Infancy and Childhood, 6th edition, vol. 2. Philadelphia: WB Saunders Company, 2003. 2 pages.

Naumov GN, Wilson SM, MacDonald IC, et al. Cellular expression of green fluorescent protein, coupled with high-resolution in vivo videomicroscopy, to monitor steps in tumor metastasis. J Cell Sci 1999; 112: 1835-42.

Nery, S., et al., "Sonic hedgehog contributes to oligodendrocyte specification in the mammalian forebrain", 2001, Development 128(4):527-540.

Nicholas, A.P. Database BIOSIS, Accession No. 2002: 2780, In vitro neuronal cell death mediated by alpha-1 A/D adrenoceptors. Society of Neuroscience Abstracts. 2001, vol. 27, No. 2, pp. 2141. Abstract.

Novak et al. In vivo flow cytometer for real-time detection and quantification of circulating cells, Optical Letters, 29 (1): 77-79 (Jan. 1, 2004).

Ntziachristos, V., et al., "Visualization of antitumor treatment by means of fluorescence molecular tomography with an annexin V-Cy5.5 conjugate", 2004, Proc Natl Acad Sci USA 101(33):12294-12299.

Nyvold C, Madsen HO, Ryder LP, et al. Precise quantification of minimal residual disease at day 29 allows identification of children with acute lymphoblastic leukemia and an excellent outcome. Blood 2002; 99: 1253-8.

Osella-Abate, S., et al., "Expression of apoptosis markers on peripheral blood lymphocytes from patients with cutaneous T-cell lymphoma during extracorporeal photochemotherapy", 2001, J Am Acad Dermatol 44(1):40-47.

Ost V, Neukammer J, Rinneberg H. Flow cytometric differentiation of erythrocytes and leukocytes in dilute whole blood by light scattering. Cytometry 1998; 32: 191-7.

Otten G, Loken M. Two color light scattering identifies physical differences between lymphocyte subpopulations. Cytometry 1982; 3: 182-7.

Padera TP, Kadambi A, di Tomaso E, et al. Lymphatic metastasis in the absence of functional intratumor lymphatics. Science 2002; 296: 1883-6.

Perelman L, Backman V, Wallace M, et al. Observation of periodic fine structure in reflectance from biological tissue: A new technique for measuring nuclear size distribution. Phys Rev Let 1998; 80:627-30.

Petrovsky, A., et al, "Near-infrared fluorescent imaging of tumor apoptosis", 2003, Cancer Research 63(8):1936-1942.

Potter MN, Steward CG, Oakhill A. The significance of detection of minimal residual disease in childhood acute lymphoblastic leukaemia. Br J. Haematol 1993; 83: 412-8.

Racila E, Euhus D, Weiss AJ, et al. Detection and characterization of carcinoma cells in the blood. Proc Natl Acad Sci U S A 1998; 95: 4589-94.

Rajadhyaksha et al., "Video-rate confocal scanning laser microscope for imaging human tissues in vivo," Appl Optics, 38(10): 2105-2115 (1999).

Reed, J., "Dysregulation of apoptosis in cancer", 1999, J Clin Oncol 17(9):2941-2953.

Rich, T., et al., "Defying death after DNA damage", 2000, Nature 407(6805):777-783.

Saito, T., et al., "Spontaneous ex vivo apoptosis of peripheral blood mononuclear cells in patients with head and neck cancer", 1999, Clinical Cancer Research 5(6):1263-1273.

San Miguel JF, Martinez A, Macedo A, et al. Immunophenotyping investigation of minimal residual disease is a useful approach for predicting relapse in acute myeloid leukemia patients. Blood 1997; 90: 2465-70.

Savill, J., et al., "Corpse clearance defines the meaning of cell death", 2000, Nature 407(6805):784-788.

Schellenberger, E.A., et al., "Optical imaging of apoptosis as a biomarker of tumor response to chemotherapy", 2003, Neoplasia (New York) 5(3):187-192.

Shapiro H Practical Flow Cytometry. New York: Alan R. Liss, Inc., 1985. 2 pages.

Siddiqua A, Chendil D, Rowland R, et al. Increased expression of PSA mRNA during brachytherapy in peripheral blood of patients with prostate cancer. Urology 2002; 60: 270-5.

Smith M, Arthur D, Camitta B, et al. Uniform approach to risk classification and treatment assignment for children with acute lymphoblastic leukemia. J Clin Oncol 1996; 14: 18-24.

[No Author Listed] Cancer Incidence and Survival among Children and Adolescents: United States SEER Program, 1975-1995. National Cancer Institute, 1999. 2 pages.

[No Author Listed] Facts and Figures. National Institute of Allergy and Infectious Diseases, 2004. 4 pages.

[No Author Listed] Handbook of biological confocal microscopy, 2nd edition. New York: Plenum Press, 1995. 2 pages.

[No Author Listed] SEER Cancer Statistics Review, 1975-2001. In: L. Ries, M. Eisner, C. Kosary, B. Hankey, B. Miller, L. Clegg, A. Mariotto, E. Feuer, and E. B. (eds). (eds.). Bethesda, MD, http://seer.cancer.gov/csr/1975 2001/: National Cancer Institute, 3 pages.

[No Author Listed] Surveillance, Epidemiology and End Results (SEER) Program. National Cancer Institute, 1975-2000. http://seer/cancer.gov/. Last accessed Aug. 15, 2005. 2 pages.

Alt, Clemens, "Advances in in vivo flow cytometry," Tufts University, Biomedical Engineering Department Fall 2005 Seminar Series, XP002493305, Nov. 6, 2006.

(56) References Cited

OTHER PUBLICATIONS

Aotake, T., et al., "Changes of angiogenesis and tumor cell apoptosis during colorectal carcinogenesis", 1999, Clin Cancer Res 5(1):135-142.

Backman V, Gopal V, Kalashnikov M, et al. Measuring cellular structure at submicron scale with light scattering spectroscopy. IEEE J Sel Top Quantum Electron 2001; 7: 887-93.

Backman V, Gurjar R, Badizadegan K, et al. Polarized light scattering spectroscopy for quantitative measurement of epithelial cellular structures. IEEE J Sel Top Quantum Electron 1999; 5: 1019-26.

Bassan R, Gatta G, Tondini C, Willemze R. Adult acute lymphoblastic leukeamia. Crit Rev Onc Hematol 2004; 50: 223-61.

Bedner, E., et al., "High affinity binding of fluorescein isothiocyanate to esosinophils detected by laser scanning cytometry: a potential source of error in analysis of blood samples utilizing fluorescein-conjugated reagents in flow cytometry", 1999, Cytometry 36(1):77-82.

Berne BJ, Pecora R Dynamic Light Scattering with Applications to Chemistry, Biology, and Physics Dover (2000). New York: Dover Publications, 2000. 2 pages.

Bigio I, Bown S, Briggs G, et al. Diagnosis of breast cancer using elastic-scattering spectroscopy: preliminary clinical results. J Biomed Opt 2000; 5: 221-8.

Blankenberg, F.G., et al., "Imaging cyclophosphamide-induced intramedullary apoptosis in rats using 99mTc-cradiolabeled annexin", 2001, Journal of Nuclear Medicine 42(2):309-316.

Bolay H, Reuter U, Dunn AK, Huang Z, Boas DA, Moskowitz MA. Intrinsic brain activity triggers trigeminal meningeal afferents in a migraine model. Nat Med 2002; 8: 136-42.

Borenstein J, Terai H, King K, Weinberg E, Kaazempur-Mofrad M, Vacanti J. Microfabrication technology for vascularized tissue engineering. Biomedical Microdevices 2002; 4:3: 167-75.

Brisco MJ, Condon J, Hughes E, et al. Outcome prediction in childhood acute lymphoblastic leukaemia by molecular quantification of residual disease at the end of induction. Lancet 1994; 343: 196-200.

Brooks, P.C., et al., "Integrin alpha v beta 3 antagonists promote tumor regression by inducing apoptosis of angiogenic blood vessels", 1994, Cell 79(7):1157-1164.

Buller G. Database BIOSIS, Accession No. 2005; 535990, Monomeric Cyanine dye permeability correlated with annexin-V staining on apoptotic cells using flow cytometry. FASEB Journal, Mar. 7, 2005, vol. 19, No. 5, Suppl. S, Part 2, pp. A1673 Abstract.

Calvi LM, Adams GB, Weibrecht KW, et al. Osteoblastic cells regulate the haematopoietic stem cell niche. Nature 2003; 425: 841-6.

Carbonari, M., et al., "Detection and characterization of apoptotic peripheral blood lymphocytes in human immunodeficiency virus infection and cancer chemotherapy by a novel flow immunocytometric method", 1994, Blood 83(5):1268-1277.

Cave H, van der Werff ten Bosch J, Suciu S, et al. Clinical significance of minimal residual disease in childhood acute lymphoblastic leukemia, European Organization for Research and Treatment of Cancer—Childhood Leukemia Cooperative Group. N EnglJ Med 1998; 339: 591-8.

Cheng T, Rodrigues N, Shen H, et al. Hematopoietic stem cell quiescence maintained by p21cip1/waf1. Science 2000; 287: 1804-8.

Coustan-Smith E, Behm FG, Sanchez J, et al. Immunological detection of minimal residual disease in children with acute lymphoblastic leukaemia. Lancet 1998; 351: 550-4.

Coustan-Smith E, Sancho J, Hancock ML, et al. Clinical importance of minimal residual disease in childhood acute lymphoblastic leukemia. Blood 2000; 96: 2691-6.

Coustan-Smith E, Sancho J, Hancock ML, et al. Use of peripheral blood instead of bone marrow to monitor residual disease in children with acute lymphoblastic leukemia. Blood 2002; 100: 2399-402.

Cummings, M.C., "Apoptosis", 1997, Am J Surg Pathol 21(1):88-101.

de Grooth B, Terstappen L, Pupples G, Greve J. Light-scattering polarization measurements as a new parameter in flow cytometry. Cytometry 1987; 8: 539-44.

Dodd SJ, Williams M, Suhan JP, Williams DS, Koretsky AP, Ho C. Detection of single mammalian cells by high-resolution magnetic resonance imaging. Biophys J 1999; 76: 103-9.

Dubey P, Su H, Adonai N, et al. Quantitative imaging of the T cell antitumor response by positron-emission tomography. Proc Natl Acad Sci U S A 2003; 100: 1232-7.

Dunn AK, Bolay H, Moskowitz MA, Boas DA. Dynamic imaging of cerebral blood flow using laser speckle. J Cereb Blood Flow Metab 2001; 21: 195-201.

Dunn AK, Devor A, Bolay H, et al. Simultaneous imaging of total cerebral hemoglobin concentration, oxygenation, and blood flow during functional activation. Opt Lett 2003; 28: 28-30.

Durrieu, F., et al., "Caspase activation is an early event in anthracycline-induced apoptosis and allows detection of apoptotic cells before they are ingested by phagocytes", 1998a, Exp Cell Res 240(2):165-175.

Ek O, Gaynon P, Zeren T, Chelstrom LM, Myers DE, Uckun FM. Treatment of human B-cell precursor leukemia in SCID mice by using a combination of the anti-CD19 immunotoxin B43-PAP with the standard chemotherapeutic drugs vincristine, methylprednisolone, and L-asparaginase. Leuk Lymphoma 1998; 31: 143-9.

Ek, O., et al., "Combined therapeutic efficacy of the thymidylate synthase inhibitor ZD1694 Tomudex) and the immunotoxin B43(anti-CD 19)-PAP in a SCID mouse model of human B-lineage acute lymphoblastic leukemia", 1998b, Leuk Lymphoma28(5-6):509-514.

Fadeel, B., "Apoptosis in human disease: a new skin for the old ceremony?", 1999, Biochem Biophys Res Commun 266(3):699-717.

Fidler I. Metastasis: quantitative analysis of distribution and fate of tumor emboli-labeled with .sup.T25I-5-lodo-2'-deoxyuridine. J Natl Cancer Inst 1970; 45: 773-82.

Fidler I. The pathogenesis of cancer metastasis: the 'seed and soil' hypothesis revisited. Nature Rev Cancer 2003; 3: 453-8.

Ford AM, Fasching K, Panzer-Grumayer ER, Koenig M, Haas OA, Greaves MF. Origins of "late" relapse in childhood acute lymphoblastic leukemia with TEL-AML1 fusion genes. Blood 2001; 98: 558-64.

Fournier M, Gireau A, Chretien MC, et al. Laboratory evaluation of the Abbott Cell DYN 3500 5-part differential. Am J Clin Pathol 1996; 105: 286-92.

Gaiano, N., "A method for rapid gain-of function studies in the mouse embryonic nervous system", 1999, Nat Neurosci 2(9):812-819.

Gaiano, N., "Radial glial identity is promoted by Notch1 signaling in the murine forebrain", 2000, Neuron 26 (2):395-404.

Georgakoudi I, Jacobson B, Van Dam J, et al. Fluorescence, reflectance and light scattering spectroscopy for evaluating dysplasia in patients with Barrett's esophagus. Gastroenterol 2001; 120: 1620-9.

Georgakoudi I, Sheets EE, Muller MG, et al. Tri-Modal Spectroscopy for the detection and characterization of cervical pre-cancers in vivo. Am J Obstet Gynecol 2002; 186: 374-82.

Groner et al., "Orthogonal polarization spectral imaging: a new method for study of the microcirculation," Nat Med, 5(10):1209-12 (Oct. 1999).

Gurjar RS, Backman V, Pe relman LT, et al. Imaging human epithelial properties with polarized light-scattering spectroscopy. Nat Med 2001; 7: 1245-8.

Handin R, Lux S, Stossel T Blood: Priniciples and Practice of Hematology, 2nd edition. Philadelphia: Lippincott Williams and Wilkins, 2003. 2 pages.

He et al. In vivo quantitation of rare circulating tumor cells by multiphoton intravital flow cytometry 104 (28): 11760-11765 (Jul. 2007).

Herschman, H.R., "Molecular imaging: looking at problems, seeing solutions", 2003, Science 302(5645):605-608.

\* cited by examiner

IN VIVO FLOW CYTOMETRY BASED ON CELLULAR AUTOFLUORESCENCE

RELATED APPLICATION

The present application claims priority to U.S. application Ser. No. 12/867,141, filed Nov. 4, 2010 and issued as U.S. Pat. No. 8,574,859 on Nov. 5, 2013, international application No. PCT/US09/38567, filed on Mar. 27, 2009, and provisional application No. 61/039,891, filed on Mar. 27, 2008.

BACKGROUND

The present invention relates generally to methods and systems for performing flow cytometry, and more particularly to such methods and systems that allow performing in-vivo flow cytometry in a live subject without extracting blood.

Many current techniques for detecting and quantifying various cell types circulating within a subject require extracting a blood sample from the subject followed by analysis of the extracted blood. For example, one such conventional method includes withdrawing a blood sample, fluorescently labeling specific cell populations ex vivo with antibody-targeted fluorescent markers, and passing those cells through a flow stream to be interrogated by a light source (typically a laser). Fluorescence and light scattering signals emitted, or reemitted, by the cells in response to the interrogating light can be employed to determine the types and the number of cells. Automated hematology analyzers can separate and count blood cell populations based on their size/volume characteristics in addition to their light scattering properties. Another blood analysis method, known as hemocytometry, is based on counting cells against a grid while being viewed with a microscope.

These techniques, though useful, require invasive blood withdrawal and hence are not particularly suited for continuous, real-time monitoring of the circulation. Further, blood withdrawal can be difficult in certain patient populations, e.g., children and psychiatric patients. In addition, such blood withdrawal can expose patients to various risks, such as infection and/or anemia. For example, in patients with low blood volume (e.g., newborns and premature infants), blood loss due to phlebotomy for common tests can equal as much as 45% of the total blood volume. Hence, diagnostic blood withdrawal is among the leading causes of anemia in neonates, which can lead to the need for frequent transfusion or erythropoietin treatment. Further, for monitoring patients for potential infection or in diseases such as leukemia and other types of cancer, frequent monitoring of the white blood cell count (WBC) can be beneficial but is currently not practical due to the frequency of blood withdrawal required. Additionally, blood withdrawal can be dangerous in immune-compromised patients, such as AIDS patients, transplant patients, or patients undergoing chemotherapy, as the skin penetration for extracting blood carries an inherent risk of infection.

Some methods for performing in-vivo flow cytometry have also been proposed previously. These methods typically utilize fluorescent antibodies or fluorescent proteins, such as green and red fluorescent proteins (e.g., GFP and DsRed), for labeling cells. However, fluorescent antibodies and fluorescent proteins are not approved for human use and require either genetic manipulation or intravenous injection. As such, the applicability of such methods can be limited.

Accordingly, there is a need for improved methods and systems for performing flow cytometry in vivo, and particularly for such methods and systems that would allow non-invasive, real-time, continuous monitoring of cell populations in circulating blood.

SUMMARY

In one aspect, the present invention provides a method of performing flow cytometry, which comprises illuminating at least a portion of blood circulating through a live subject with radiation so as to excite one or more intrinsic cellular fluorophores of a plurality of circulating cells, and detecting fluorescence radiation emitted by the excited fluorophores. The detected fluorescence radiation can be utilized to count the cells emitting the radiation. More specifically, the detected fluorescence radiation can be analyzed to obtain information regarding one or more cell types of interest, such as, their presence in the circulatory system, their absolute concentration in the blood (number of cells of a cell type within a predefined volume of blood), changes in concentration over time (e.g., as a result of treatment or increasing immune response to an infection/disease), absolute and relative concentrations of subpopulations of cells, and the velocity of blood flow and cell size.

In a related aspect, the illumination step in the above method can cause multi-photon excitation of one or more of the fluorophores. In some cases, a plurality of laser pulses can be focused into a volume of the circulating blood at sufficiently high irradiance so as to cause multi-photon excitation (e.g., two-photon or three-photon excitation) of at least some of the intrinsic fluorophores. For example, the laser pulses can have temporal durations less than about 1 nanosecond, e.g., in a range of about 1 femtosecond to about 900 picoseconds, and more preferably in a range of about 10 femtoseconds to about 300 femtoseconds. In some cases, such laser pulses can be focused into the circulating blood at a numerical aperture so as to provide a focal volume characterized by a diameter, e.g., in a range of about 0.2 to about 10 microns.

A variety of intrinsic cellular fluorophores can be employed. Some examples include, without limitation, amino acids such as tryptophan, the reduced form of nicotinamide adenine dinucleotide (NADH), flavin adenine dinucleotide (FAD), and porphyrins.

Fluorophores can be excited by both one-photon excitation and multi-photon (e.g., two- and three-photon) excitation processes. Such one-photon and multi-photon excitations can be applied concurrently to the same or different blood volumes. Alternatively, they can be applied in different temporal intervals to a subject's circulating blood to derive information regarding one or more cell types of interest.

In another aspect, a method of performing flow cytometry is disclosed that includes in vivo labeling (that is, labeling the cells while they are in the blood circulating in the subject) one or more circulating cells of a subject with an exogenous fluorophore, illuminating the labeled cells in vivo with radiation (that is, illuminating the cells while they are circulating in the subject) so as to cause multi-photon excitation of the fluorophore, detecting the fluorescence radiation emanating from the fluorophores of labeled cells in response to the multi-photon excitation, and analyzing the detected fluorescence radiation to count the cells emitting the radiation, and more specifically to obtain information about the labeled cells, e.g., the concentration, size, or type of one or more labeled cells of interest.

In some embodiments, the exogenous fluorophore is tetracycline, an FDA approved antibiotic that can be orally administered to a patient. Within the blood, tetracycline molecules can selectively label leukocytes via accumulation in their mitochondria. Tetracycline is a fluorescent molecule that can absorb radiation in the ultraviolet (UV) region at about 376 nm and can emit fluorescence radiation at a wavelength of about 516 nm. Rather than using UV radiation to excite tetracycline in the circulating leukocytes, in many embodiments, multi-photon excitation (e.g., two-photon excitation) of tetracycline, for example, two-photon excitation at about 752 nm, can be employed to avoid exposing the subject to damaging UV radiation.

In another aspect, a method of performing flow cytometry is disclosed that includes illuminating at least a portion of blood circulating through a live subject with radiation so as to excite one or more endogenous cellular fluorophore, e.g., tryptophan, NADH, or FAD, of one or more circulating cells at two or more different excitation wavelengths, detecting fluorescence radiation emitted by the excited fluorophores of the cells in response to said two or more excitation wavelengths, and comparing the detected intensity of fluorescence emitted in response to one excitation wavelength with detected intensity of fluorescence emitted in response to at least another excitation wavelength to determine the type of cells generating the fluorescence radiation.

In some embodiments, one excitation wavelength can be about 295 nm and another of excitation wavelengths can be about 255 nm. In some embodiments, the flourophores can be excited via multi-photon excitation for at least one of the excitation wavelengths.

In another aspect, a method of performing flow cytometry is disclosed that includes exciting an intrinsic fluorophore of a cell circulating in vasculature of a live subject at a first interrogation site to elicit fluorescence radiation from the cell, detecting the fluorescence radiation, and utilizing the fluorescence radiation to trigger interrogation of the cell at another interrogation site. In some embodiments, the step of utilizing the detected fluorescence can include interrogating the cell at another interrogation site after a predetermined time period from the detection of the fluorescence. For example, interrogating the cell at another interrogation site can include obtaining a fluorescence or scattering signature of the cell or an image of the cell.

In another aspect, an apparatus for performing flow cytometry is disclosed that includes a source for generating radiation suitable for causing multi-photon excitation of one or more fluorophores, and an optical system for directing the radiation onto a portion of a subject's circulatory system so as to cause multi-photon excitation of one or more fluorophores within or bound to one or more cells circulating in the subject. The apparatus can further include a detector for detecting fluorescence radiation emitted by the fluorophores in response to the multi-photon excitation, and an analysis module for analyzing the detected fluorescence radiation.

Further understanding of the invention can be obtained by reference to the following description in conjunction with the associated drawings, which are briefly described below.

DETAILED DESCRIPTION

The present invention generally provides methods and systems for performing in vivo flow cytometry by using blood vessels as flow chambers through which flowing cells can be monitored in a live subject in vivo (that is, while the blood is flowing through the live subject) without the need for withdrawing a blood sample. In some embodiments, one or more blood vessels are illuminated with radiation so as to cause a multi-photon excitation of an exogenous fluorophore that was previously introduced into the subject to label one or more cell types of interest. The emission of fluorescence radiation from such fluorophores in response to the excitation can be detected and analyzed to obtain information regarding the labeled cell type, as discussed further below. The term "fluorophore" is known in the art and is used herein to refer to a compound that can emit fluorescence radiation, e.g., in response to an optical excitation. Further, the in vivo excitation of a fluorophore refers to exciting the fluorophore while it is circulating through a live subject's vasculature.

In some other embodiments, rather than utilizing an exogenous fluorophore, endogenous (intrinsic) cellular fluorescence can be employed for in vivo flow cytometry. For example, one or more naturally occurring cellular fluorophores, e.g., tyrosine, tryptophan, the reduced form of nicotinamide adenine dinucleotide (NADH), flavin adenine dinucleotide (FAD), and porphyrins such a protoporphyrin IX (PpIX), can be excited in vivo by illuminating one or more blood vessels with excitation radiation to cause those fluorophores to emit fluorescence radiation. The emitted fluorescence radiation can be detected and analyzed, e.g., in a manner discussed in more detail below, to obtain information about one or more cell types of interest. In some embodiments, such excitation of a naturally occurring fluorophore can be achieved via a multi-photon excitation process. The terms "light" and "radiation" are used interchangeably herein to refer to electromagnetic radiation.

Figure 1:
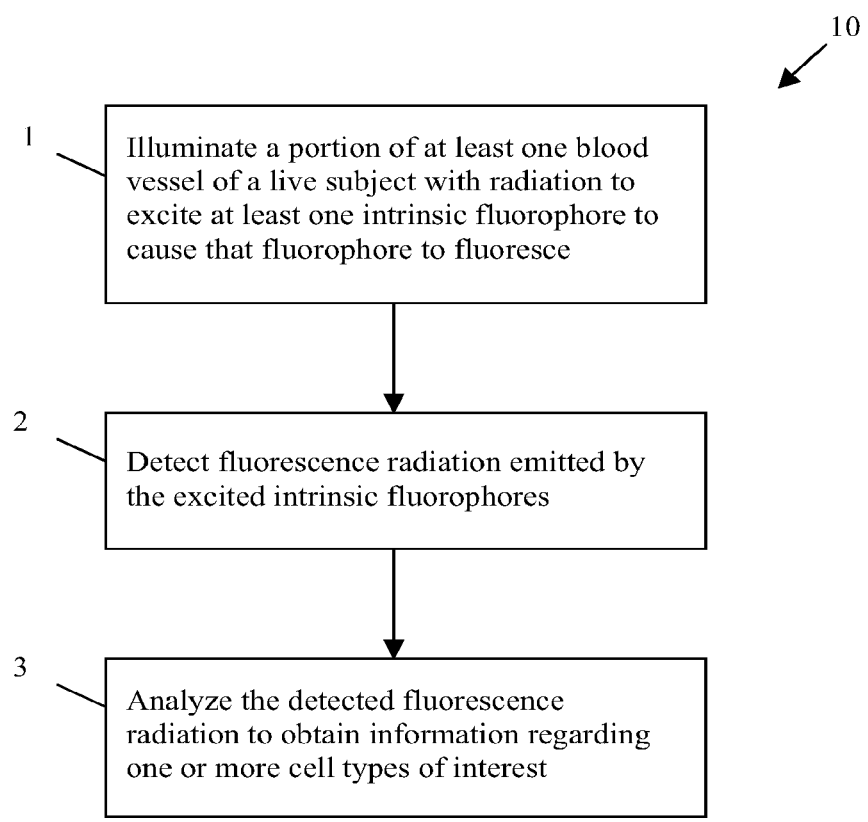
FIG. 1 is a flow chart depicting various steps in one embodiment of a method according to the teachings of the invention for performing flow cytometry using intrinsic fluorophores.

By way of further illustration and with reference to a flow chart 10 of FIG. 1, in one exemplary embodiment of a method for performing flow cytometry in accordance with the teachings of the invention, in a step 1, a portion of at least one blood vessel of a live subject (e.g., a patient) is illuminated with radiation to excite at least one intrinsic, naturally occurring cellular fluorophore causing that fluorophore to fluoresce. The terms "naturally occurring cellular fluorophore(s)" and "intrinsic cellular fluorophore(s)" are used herein interchangeably to refer to a compound, e.g., an amino acid or an enzyme cofactor, that is naturally present in a cell and can be excited to fluoresce. In many embodiments, multi-photon, rather than single-photon, excitation is employed for exciting intrinsic cellular fluorophores. Further, as discussed in more detail below, in some embodiments, multi-photon excitation can be employed to excite exogenous fluorophores bound to or contained within cells to elicit fluorescence radiation from those cells, which can then be analyzed to obtain information about those cells.

Such multi-photon excitation advantageously allows the use of visible or infrared radiation, rather than ultraviolet (UV) radiation, for eliciting fluorescence radiation from naturally occurring cellular fluorophores, thus avoiding damage to the DNA of cells that UV radiation could potentially cause. Further, visible and infrared radiation used for multi-photon excitation can penetrate deeper into tissue than UV radiation due to the decreased radiation absorption and scattering in tissue in these wavelength ranges. The greater penetration depth of the radiation in turn allows for probing of blood flowing through larger blood vessels or blood vessels located at greater depths below the tissue surface.

In many embodiments, the excitation radiation is focused onto a focal volume within the tissue (e.g., onto blood flowing through a vessel) such that the radiation intensity is sufficiently high within the focal volume to cause multi-photon excitation of one or more naturally occurring fluorophores. In other words, the electric field within the focal volume is large enough to cause multi-photon excitation of the fluorophore(s). The radiation intensity (and consequently the associated electric field) is, however, much lower in the regions outside the focal volume, leading to a significant decrease in the probability of multi-photon excitation in those regions. In this manner, only the cells within the illuminated focal volume will be excited, while other cells and tissue lying outside the focal volume will not. Multi-photon illumination therefore allows excitation of cells of interest within the vasculature without harming the surrounding tissue.

As noted above, in some cases the naturally occurring cellular fluorophores that can be excited include tyrosine, tryptophan, NADH, FAD, and protoporphyrin IX. By way of example, tryptophan, an amino acid that occurs in proteins, has an absorption maximum at a wavelength of about 280 nm and a fluorescence emission maximum at about 350 nm. NADH, which is an enzyme cofactor that participates in cell metabolism, has absorption and emission spectra peaks at approximately 340 nm and 460 nm, respectively. FAD, another enzyme cofactor involved in metabolism, has a radiation absorption peak near 450 nm and a fluorescence emission peak around 525 nm. As discussed above, rather than utilizing UV radiation for exciting such naturally occurring fluorophores via single photon excitation, in many embodiments multi-photon excitation of the fluorophores is employed. For example, illumination wavelengths at about 560 nm, 680 nm, and/or 900 nm can be utilized to excite tryptophan, NADH, and/or FAD, respectively, via two-photon excitation.

Referring again to the flow chart of FIG. 1, in step 2, the emitted fluorescence from one or more excited naturally occurring fluorophores is detected. In step 3, the detected fluorescence radiation is analyzed to obtain information regarding one or more cell types of interest. By way of example, the detection of intrinsic fluorescence can indicate the presence of certain cell types (e.g., cancer cells or white blood cells).

Furthermore, fluorescence signal intensities from the intrinsic fluorophores can be used to distinguish between different cell populations. For example, there is evidence that intrinsic fluorophores are distinctively distributed among leukocyte sub-populations. While monocytes emit approximately equal tryptophan and NADH fluorescence per cell, neutrophils exhibit much stronger tryptophan than NADH fluorescence signal. Hence, in some embodiments, white blood cell sub-populations can be identified via the tryptophan-to-NADH (Trp/NADH) fluorescence intensity ratio. In this case, neutrophils can be distinguished from monocytes via their higher Trp/NADH fluorescence intensity ratio.

In some cases, the fluorescence emission from one or more endogenous fluorophores at different excitation wavelengths can be analyzed to determine the cell type and sub-population contributing to the detected fluorescence. For example, there is evidence that endogenous fluorescence intensity in agranulocytes (lymphocytes and monocytes) is stronger upon excitation at 295 nm than excitation at 255 nm. In granulocytes (neutrophils, eosinophils, basophils), on the other hand, the endogenous fluorescence intensity remains almost equal at those two excitation wavelengths (i.e., at 295 nm and 255 nm). Hence, cells exhibiting a large ratio of emission at 295 nm excitation relative to emission at 255 nm excitation (Fluor(295)/Fluor(255)) can be identified as agranulocytes. Those cells exhibiting a Fluor(295)/Fluor(255) ratio on the order of one can be identified as granulocytes. The methods of analyzing the detected fluorescence radiation to identify cell types and sub-populations are not restricted to the above examples.

The analysis of the detected fluorescence radiation is not restricted to the analysis of its intensity. Other spectroscopic parameters, such as spectral widths and shapes of the fluorescence signals can also be helpful in selectively identifying cell populations. Cell morphology and size can also aid in the discrimination of the cell populations. Cell size and morphology (e.g., the shape of the cell) are characteristic to certain populations of cells and can be examined by measuring the light scattering in addition to fluorescence. For example, neutrophils are about 10 µm in diameter and have a nucleus with multiple lobes, while lymphocytes are smaller than 10 µm in diameter, with a smooth shape and a large, round nucleus. Yet another population, monocytes, are about 15 µm in diameter with an irregular shape and a comparatively small nucleus. Light scattered from these cells can be used to distinguish one population from another. In some cases, the fluorescence radiation can be analyzed to determine a size of the cell(s) emitting the fluorescence radiation, which can in turn be employed to determine the type of those cells.

In some embodiments, the intensity of each detected fluorescence signal is compared to a threshold intensity, and the signal is considered as emanating from a cell only if the fluorescence intensity exceeds the threshold. Further, in some cases, for each fluorescence signal (fluorescence peak) emanating from a cell, a signal width can be determined. In many embodiments, a signal width can be defined as full width at half maximum (FWHM) of the signal's intensity profile. Those having ordinary skill in the art appreciate that alternative measures of a signal's width, such as half width at half maximum, can also be utilized. In some cases, only the signals having widths that comply with a predefined criterion can be retained for analysis and the others can be rejected. Thus, one or more fluorescence signals having widths that are much smaller than what would be reasonably expected for an authentic fluorescence signal emanating from a cell can be rejected. When detecting fluorescence from cells circulating in an arterial vessel, for example, the signal width is typically expected to be greater than about 0.1 millisecond. Hence, signals having smaller widths can be considered as false or background noise. The signal analysis methods disclosed in U.S. Published Patent Application No. 2006/0134002 entitled "In Vivo Flow Cytometry System and Method," which is herein incorporated by reference in its entirety, can be employed in various embodiments of the invention.

Figure 2:
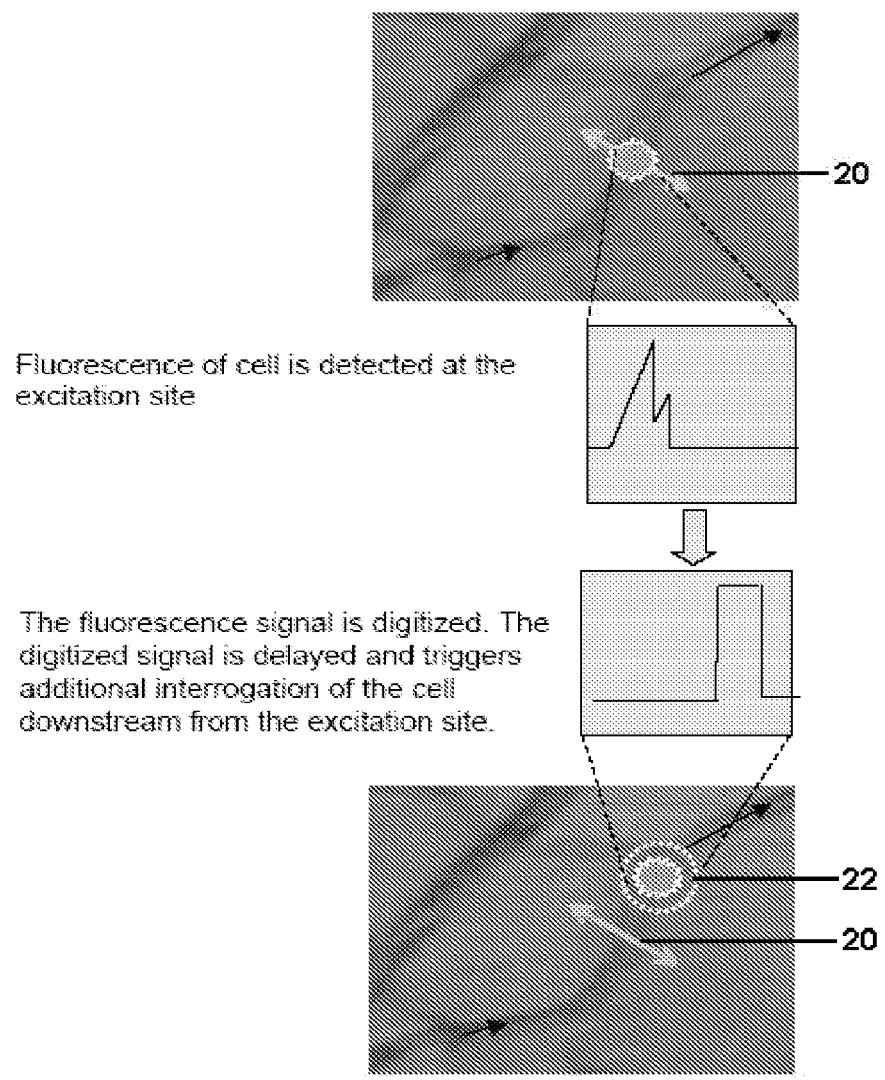
FIG. 2 schematically illustrates interrogating circulating cells at two sites, where the fluorescence radiation at one site can trigger the interrogation of the circulating cells at a downstream site.

In some embodiments, a fluorescence signal from a cell can be utilized to prompt additional interrogation of that cell downstream from the excitation site. For example, with reference to FIG. 2, when a cell passes an excitation site 20 (marked by arrows), a fluorophore of the cell can be excited to cause it to emit a fluorescence radiation signal. The fluorescence signal can then be used to trigger additional interrogation of the cell, via a variety of methods, as the cell arrives at such additional interrogation site (e.g., a location within the vasculature) 22 (marked by a dotted circle). In some cases, the additional interrogation can be triggered after a pre-determined time period from the detection of the fluorescence signal. In some cases, such a predetermine time period can be determined based on measured or estimated flow velocity of the cell within the vasculature. For example, such additional interrogation can comprise obtaining an image of the cell to directly observe its morphology and/or size and/or to determine fluorescence distribution within the cell. In another example, the additional interrogation can include obtaining a radiation scattering signature of the cell by illuminating it with suitable radiation and detecting radiation scattered by the cell in response to such illumination, e.g., by utilizing a CCD camera. By way of example, such a scattering signature of the cell can be employed to measure the cell size and/or shape. In another example, this additional interrogation site can include a spectrometer, which would allow acquisition of spectral signatures of the passing cells. Spectral signatures will yield additional information about the fluorophores within a cell, including spectral width and line shape. Such additional interrogations of the cells, performed at the initial interrogation site or at a downstream site, can aid in some cases in the discrimination of signals from different cell types.

Figure 3:
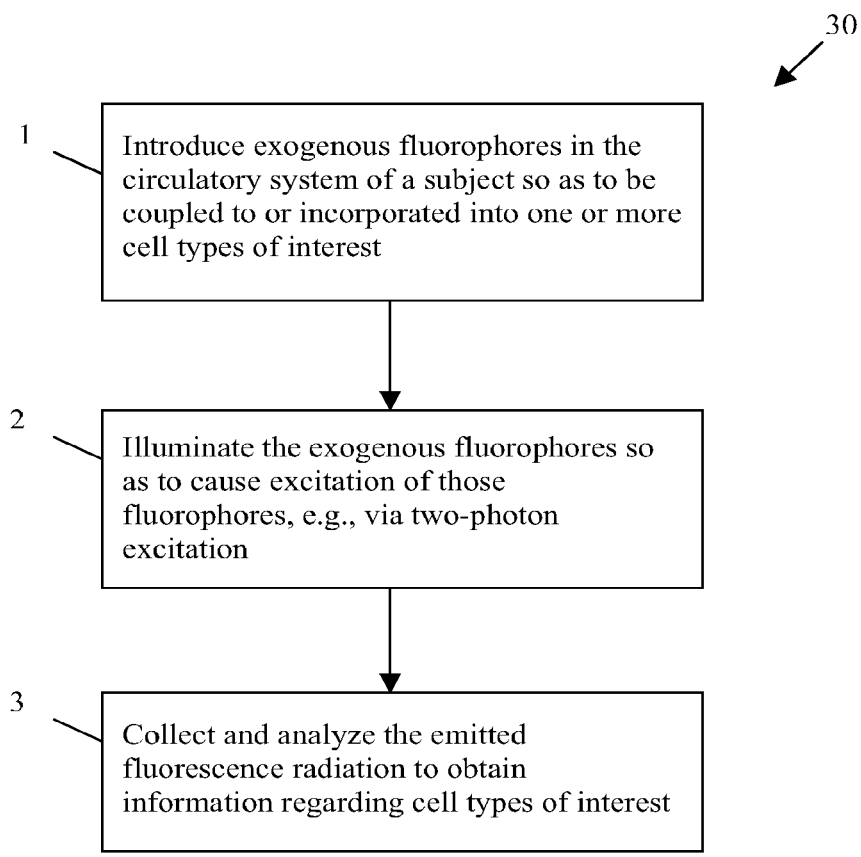
FIG. 3 is a flow chart depicting various steps in another embodiment of a method according to the teachings of the invention for performing flow cytometry using exogenous fluorophores.

With reference to the flow chart 30 shown in FIG. 3, in another embodiment for performing in vivo flow cytometry, an exogenous fluorophore can be introduced into a subject's circulatory system so as to be coupled to or incorporated into one or more cell types of interest (step 1). In step 2, those cells can be illuminated, e.g., by focusing radiation onto blood circulating through the subject, so as to cause one-photon or multi-photon excitation of those fluorophores. In step 3, the fluorescence radiation emitted by the excited fluorophores can be collected and analyzed to count the cells emitting the fluorescence radiation and more specifically to obtain information regarding the cell type(s) of interest.

By way of example, in some embodiments, tetracycline, an FDA approved antibiotic, can be administered, e.g., orally, to a subject so as to selectively label leukocytes by accumulating in the mitochondria of the cells. Tetracycline has been shown to selectively label leukocytes in ex vivo whole blood samples at a drug concentration of 10 micrograms/milliliter, a serum level that is attainable therapeutically. Tetracycline is a fluorescent molecule that absorbs radiation in the ultraviolet (UV) region at 376 nm and emits fluorescence radiation having a peak intensity at a wavelength of about 516 nm. In many embodiments, rather than using one-photon excitation, multi-photon excitation of the tetracycline taken up by circulating cells (e.g., circulating leukocytes) is employed so as to avoid exposing the cells to the ultraviolet radiation (radiation with wavelengths in a range of about 1-400 nanometers), which could cause damage to the DNA of the cells. More specifically, such multi-photon excitation allows tetracycline molecules to be excited by radiation having a wavelength which lies in the near-infrared portion of the electromagnetic spectrum (e.g., a two-photon excitation wavelength of about 752 nm).

By way of example, the fluorescence radiation from the excited endogenous fluorophores (e.g., Trp, NADH, and FAD) or tetracycline molecules can be collected and analyzed, e.g., in a manner discussed above, to derive information regarding the circulating leukocytes. For example, the fluorescence radiation can be analyzed to count the leukocytes to obtain information regarding changes to the concentration of those cells over time. Monitoring the leukocyte concentration in this manner, by either utilizing endogenous fluorescence or by labeling cells in vivo with an exogenous marker, can provide information regarding the progression of a disease (e.g., an infection or leukemia) and/or the efficacy of an applied treatment protocol. Such monitoring can be done in real-time, and as many times as needed without extracting blood from the subject. Such non-invasive monitoring can help determine, e.g., if a subject has an infection and/or if the infection is responding to treatment. It can also be utilized to screen for leukocyte-related diseases in children (such as leukemia), to monitor patients with known chronic leukemia for the onset of blast crisis, or to monitor treatment outcomes in immune-compromised patients, without the risk of infection that can accompany blood extraction.

In some embodiments in which the intrinsic cellular fluorophores are employed for in-vivo flow cytometry, one or more of those fluorophores can be excited via multi-photon excitation and one or more others of those fluorophores can be excited via single-photon excitation. Such single-photon and multi-photon excitations can be done concurrently, e.g., by utilizing the in-vivo flow cytometry system shown in FIG. 5 and discussed below, within the same or different circulating blood volumes. Further, in some cases, the single-photon and multi-photon excitations are performed at different sites, e.g., different portions of a blood vessel. In some cases, the excitations can be synchronized (e.g., one excitation can trigger the performance of the other with a pre-defined delay) so as to correspond to substantially the same blood volume as the blood moves through a vessel from one site to the other.

The methods of the invention for performing in-vivo flow cytometry can be practiced by employing a variety of blood vessels in a subject. By way of example, in some cases, one or more blood vessels can be illuminated to excite intrinsic and/or exogenous fluorophores that are bound to or incorporated in cells flowing through those vessels. In addition, one or more fluorophores can be probed simultaneously.

Figure 4:
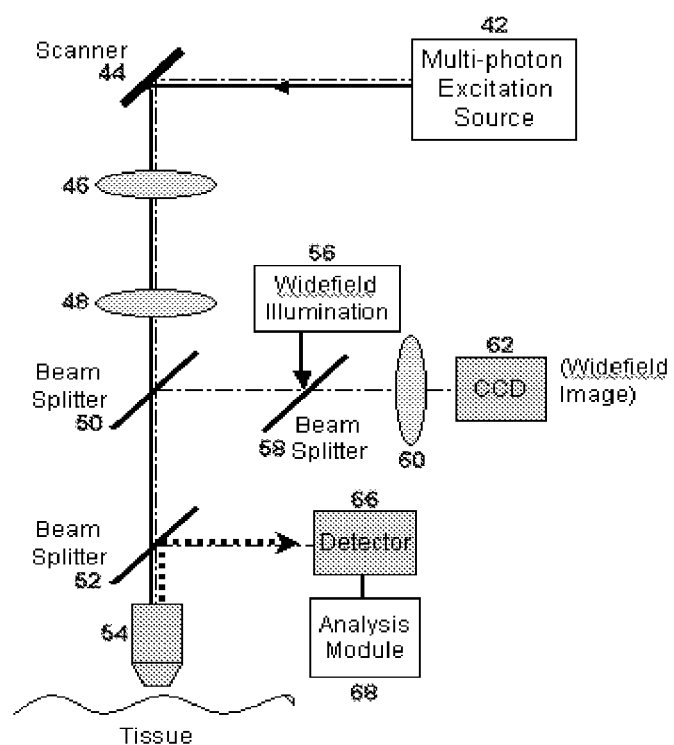
FIG. 4 schematically illustrates a system according to one embodiment of the invention for performing flow cytometry using a multi-photon excitation system.

FIG. 4 schematically depicts an embodiment of an optical system 40 for performing in vivo flow cytometry in accordance with the teachings of the invention that can be utilized to perform flow cytometry, e.g., the measurements discussed above. The system 40 includes an excitation laser 42 that generates radiation pulses having wavelengths suitable for multi-photon excitation of one or more naturally occurring fluorophores. In this case, the radiation source can generate a plurality of radiation wavelengths for multi-photon excitation of a plurality of naturally occurring fluorophores, e.g., for simultaneous excitation of tryptophan, NADH and FAD. By way of example, in some cases the radiation source can comprise different radiation emitting elements, each suited for generating radiation with different wavelengths for exciting different fluorophores (e.g., concurrently). In other cases, a single tunable source can be utilized to generate radiation at different wavelengths for exciting different fluorophores. Yet, in other cases, a broadband source can be employed. Some examples of suitable radiation sources can be, without limitation, a pulsed laser system capable of generating laser pulses with femtosecond-scale temporal durations, fiber-lasers, regenerative amplifiers, or super-continuum generating light sources that allow selection of a suitable wavelength with a tunable filter.

The system 40 further includes a scanner 44 that receives the radiation from the radiation source 42 and directs the radiation to a pair of lenses 46 and 48. The scanner 44, which can be, e.g., a galvanometer scanner, a polygon scanner, an electro-optical or acousto-optical scanner, can translate the laser beam across the diameter of a blood vessel exposed to the radiation in order to efficiently sample circulating blood across the width of the blood vessel. The pair of lenses 46 and 48 form a telecentric relay to ensure that the stationary spot on the scanner is imaged directly onto the entrance pupil of focusing optic 54. In this embodiment, the focusing optic 54 comprises a microscope objective that focuses the excitation radiation onto a blood vessel within the tissue.

A light emitting diode 56 provides wide field illumination of the tissue for visualization of the vasculature within it. More specifically, the wide field illumination radiation is reflected by a beam splitter 58 to be transmitted to the beam splitter 50, which in turn reflects the wide field illumination radiation substantially coaxially with the radiation from the source 42 to the beam splitter 52. The wide field illumination radiation passes through the beam splitter 52 to be focused by the optic 54 onto a portion of tissue under study. The radiation reflected from the tissue in response to the wide field illumination radiation follows a return path through the beam splitters 52, 50, and 58 to be focused by a lens 60 onto a CCD camera 62. The camera 62 generates an image of the tissue under investigation including the vessel illuminated by the radiation from the source 42. This image can facilitate aligning the radiation beam from the source 42 onto a vessel.

With continued reference to FIG. 4, the excitation radiation focused by the optic 54 onto the blood flowing through a vessel causes multi-photon excitation of one or more intrinsic cellular fluorophores or exogenous fluorophores of cells passing through the focal volume. As noted above, in this embodiment, a number of such fluorophores (e.g., Trp, NADH, FAD and tetracycline) can be simultaneously, or concurrently, excited via multi-photon excitation. The fluorescence radiation emitted by the excited fluorophores is directed by the optic 54 to the beam splitter 52, which in turn reflects the fluorescence onto a detector 66. The detection signals generated by the detector 66 can be transmitted to an analysis module 68 to be analyzed, e.g., in a manner discussed above. As the fluorescence radiation can include a plurality of different wavelengths (in this case as a result of simultaneous excitation of a plurality of different fluorophores), the detector 66 can include a plurality of detector elements each of a which suited for detection of a particular fluorescence wavelength. By way of example, in some cases, a plurality of optical elements, such as beam splitters, can be employed to distribute the fluorescence radiation among such detecting elements. Alternatively, in some embodiments, each detector element can be periodically placed in the path of the fluorescence radiation to detect radiation of a particular wavelength.

Figure 5:
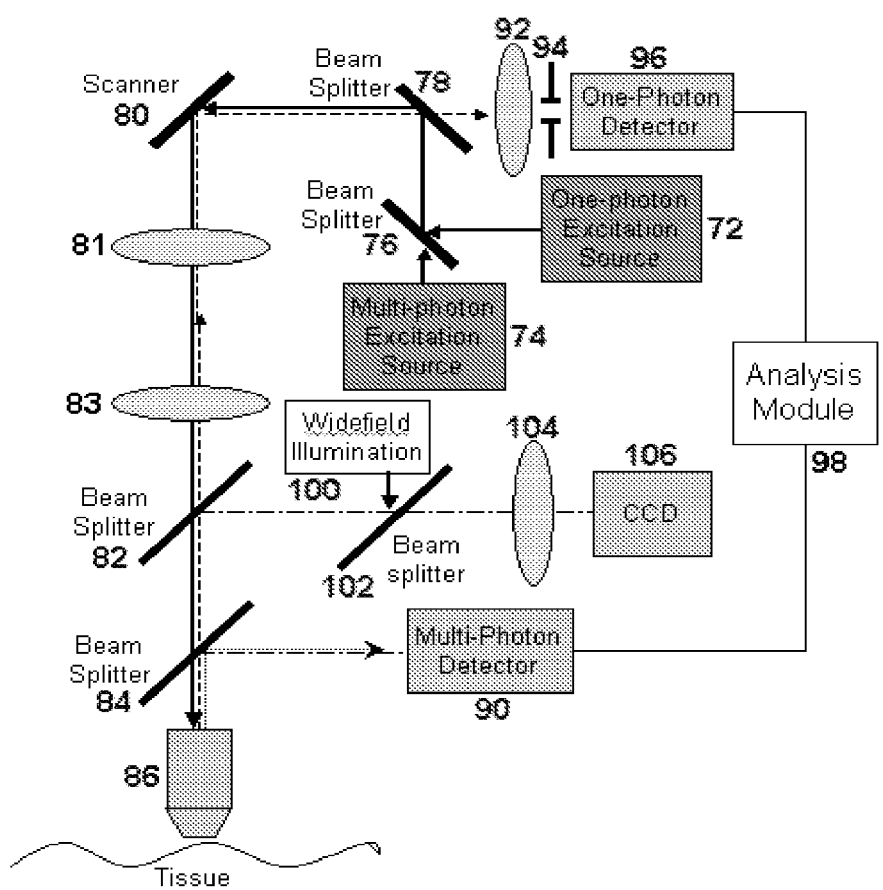
FIG. 5 schematically illustrates a system according to another embodiment of the invention for performing flow cytometry using a combined multi-photon and one-photon excitation system.

FIG. 5 schematically depicts a combined multi-photon and one-photon excitation system 70 for performing in-vivo flow cytometry in accordance with some embodiments of the invention. The system 70 includes two excitation sources 72 and 74, one of which provides radiation at one or more wavelengths suitable for multi-photon excitation of one or more fluorophores of interest and the other provides radiation at one or more wavelengths suitable for one-photon excitation of one or more fluorophores (the same as or different from the fluorophores that are subjected to multi-photon excitation).

In this embodiment, the source 72 comprises a laser providing continuous-wave (CW) radiation, though in other embodiments the source 72 can provide pulsed radiation. By way of example, the radiation source can be a CW He—Ne laser providing radiation at wavelengths of 632 to 638 nm, one of which is commercially available form Coherent of Santa Clara, Calif. Some other examples of such one-photon excitation lasers include, without limitation, gas, diode and solid-state lasers ranging from the ultra-violet to the infra-red, at wavelengths of about 266, 375, 470, 490, 514, 532, 561, 750, 830 nm. In this embodiment, the other radiation source 74 is a laser providing pulses of radiation with temporal durations less than about 1 nanosecond, e.g., pulse widths in a range of about 1 femtosecond to about 900 picoseconds, and more preferably in a range of about 10 femtoseconds to about 300 femtoseconds. By way of example, the source 74 can be a pulsed femtosecond Ti:Sapphire tunable laser, e.g., a femtosecond laser available from Spectra Physics, Mountain View Calif., U.S.A. Other examples of lasers suitable for use as the source 74 include, without limitation, a pulsed laser system capable of generating laser pulses with femtosecond-scale temporal durations, fiber-lasers, regenerative amplifiers, or super-continuum generating light sources that allow selection of a suitable wavelength with a tunable filter. Further, in this embodiment, the radiation source 74 includes a femtosecond laser for generation of femtosecond pulses, and an optical parametric amplifier (OPAL, Spectra Physics) to shift the wavelength of the femtosecond pulses, and—for multi-photon excitation of Tryptophan—a doubling crystal (Spectra Physics) that converts the near-infrared output of the OPAL to visible light.

The radiation from the sources are coupled via a beam splitter 76 to another beam splitter 78, which in turn reflects the radiation from the sources onto a coaxial path toward a scanner 80, e.g., a resonant galvanometer mirror in this case (other types of scanners such as those listed above can also be utilized). Similar to the previous embodiment, the scanner 80 can scan the radiation beams over a portion of a vessel of interest, e.g., across the diameter of a blood vessel so as to sample the entire width of the vessel. The fastest cells in an artery are estimated to move at a velocity of about 10 mm/s and the smallest leukocytes are approximately 6 microns in diameter. Hence, in many embodiments, the scan rate is at least about 1 kHz (e.g., 1.6 kHz), and preferably at least about 2 kHz (e.g., 3.2 kHz), to maximize the intersection of a radiation beam with cells across a vessel width.

With continued reference to FIG. 5, the two radiation beams are telecentrically relayed by optical elements 81 and 83 and travel coaxially through beam splitters 82 and 84 to reach a focusing optic 86 (e.g., an infinity-corrected microscope objective positioned in an inverted configuration) that focuses the radiation beams, e.g., onto blood flowing through a vessel, to cause one-photon and/or multi-photon excitations of fluorophores passing through the focal volume. In some embodiments, the numerical aperture (NA) of the focusing optic 86 in the forward direction (toward the vessel to be illuminated) can be, e.g., in a range of about 0.2 to about 1.4 (e.g., 0.8). The excitation lasers and focusing optics are generally adjusted to optimally probe the depth of the blood vessel.

The radiation beam having one or more wavelengths suitable for one-photon and multi-photon excitation of one or more fluorophores (e.g., exogenous fluorophores attached to or within one or more cell types of interest or intrinsic cellular fluorophores) causes those fluorophores passing through the focal volume to fluoresce.

The fluorescence radiation caused by one-photon and multi-photon excitations is collected by the optic 86 to be transmitted to the beam splitter 84. The beam splitter 84 reflects the fluorescence radiation corresponding to the multi-photon excitation (herein referred to as "multi-photon fluorescence") toward a multi-photon detector 90, which in this case is a photomultiplier tube (PMT), while allowing the passage of the fluorescence radiation corresponding to one-photon excitation (herein referred to as "one-photon fluorescence").

The one-photon fluorescence is, however, detected confocally relative to the one-photon excitation. The one-photon fluorescence radiation continues to travel in a direction opposite to that of the excitation radiation to pass through the beam splitters 82 and 84 to be reflected by the scanner 80 toward the beam splitter 78. The reflection of the fluorescence radiation by the scanner 80 along a reverse direction relative to the excitation direction undoes the scanning of the beam (i.e., it de-scans the beam) generating a fluorescence beam that is substantially stationary in a plane perpendicular to its propagation direction, i.e. it generates a standing spot on the confocal pinhole 94. The fluorescence beam passes through the beam splitter 78 to be focused by a lens 92 onto a confocal pinhole 94 prior to its detection by a photodetector 96, e.g., a photomultiplier tube (PMT). Such confocal detection of the one-photon fluorescence radiation advantageously allows detecting fluorescence from a selected excitation volume while minimizing interference from radiation emanating from regions outside that excitation volume. The terms "confocal detection" and "confocally detecting" are known in the art, and to the extent that any further explanation is required, they refer herein to detecting fluorescence photons in a plane that is conjugate to the plane of excitation radiation that is focused onto a selected portion of a subject's circulatory system, e.g., a vessel, to excite fluorophores passing therethrough.

The detectors 90 and 96 generate output electrical signals (e.g., output voltages) in response to the detection of fluorescence radiation, which can be sent to an analysis module 98 for recording and/or analysis. An increase in a PMT's output voltage corresponds directly to an increase in fluorescence from the sample, indicating the passage of a cell through the focal volume. Fluorescence signal peaks can be identified by suitable peak-detection algorithms, such as those discussed above, and counted to enumerate cells within a given temporal period.

As in the system shown in FIG. 4, in some implementations of the system 70, the single-photon and multi-photon detectors can be detector arrays.

Further, similar to the previous embodiment, the system 70 can provide a wide field image of the tissue for visualization of the vasculature as well as identification of blood vessel locations for measurement. More specifically, a light emitting diode (LED) 100 can provide light that is reflected via a beam splitter 102 as well as the beam splitters 82 and 84 to the optic 86, which in turn focuses the light onto an area of interest. The returning reflected and/or scattered light is focused by a lens 104 onto a CCD camera 106 that generates an image of the field of view.

Figure 6:
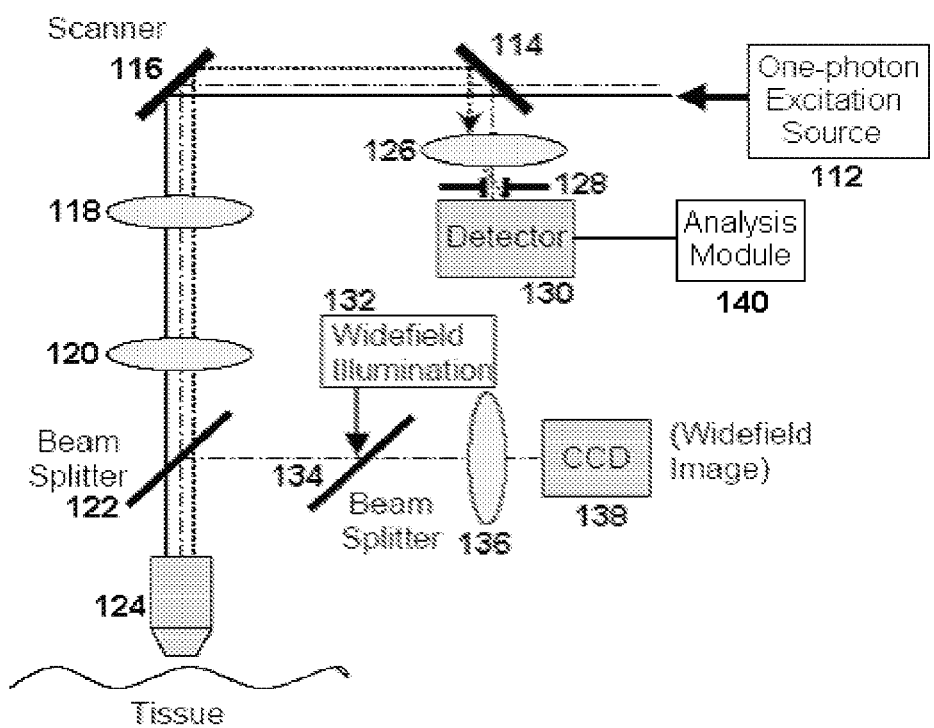
FIG. 6 schematically illustrates a system according to one embodiment of the invention for performing flow cytometry using a one-photon excitation system.

In some cases, the fluorophores (exogenous fluorophores and/or intrinsic cellular fluorophores) can be excited via one-photon excitation. Such excitation can be in conjunction with multi-photon excitation as discussed above, or could be performed without a need for multi-photon excitation. By way of illustration, FIG. 6 schematically depicts a confocal one-photon cytometry system 110 that includes an excitation radiation source 112 (e.g., a CW laser) that provides radiation suitable for one-photon excitation of one or more fluorophores. The radiation generated by the source passes through a beam splitter 114 to be directed by a scanner 116 (e.g., a galvanometer scanner) to two lenses 118 and 120 that relay the beam onto the focusing optic 124. The beam passes through another beam splitter 122 to be focused by an optic 124 onto a selected portion of a subject's tissue, e.g., blood flowing through a vessel, so as to excite one ore more fluorophores. The fluorescence radiation emitted in response to such excitation exits the tissue and is collected by the optic 124 onto a path opposite to that of the excitation radiation to be reflected by the beam splitter 114 onto the lens 126. The reflection of the fluorescence radiation by the scanner 116 along a reverse direction relative to the excitation radiation undoes the scanning and hence result in a fluorescence beam that is substantially stationary in plane orthogonal to the propagation direction. The lens 126 focuses the returning fluorescence radiation onto a confocal slit 128, which is placed in front of a detector 130. The detector 130 in turn generates electrical signals in response to the detection of the fluorescence radiation that are transmitted to an analysis module 140 to be analyzed and/or stored.

Similar to the previous embodiments, a wide field illumination source 132 can provide a light beam that is reflected by beam splitters 134 and 122 to be focused by the optic 124 onto the tissue to facilitate visualization of the vasculature. The light reflected and/or scattered by the tissue in response to such illumination is reflected by the beam splitter 122 to pass through beam splitter 134 to a lens 136. The lens 136 in turn focuses the light onto a CCD detector 138, which generates an image of the field of view.

In some cases, the one-photon excitation apparatus can be used in tandem with a multi-photon excitation apparatus, such as that shown in FIG. 4. For example, the one-photon excitation apparatus can be employed upstream or downstream from the multi-photon excitation apparatus. Alternatively, it can be used independent of the multi-photon excitation apparatus.

In some cases, an embodiment of a system for performing in vivo flow cytometry can optionally include one or more optical probes, e.g., handheld probes, that are adapted to probe sites on a patient. By way of example, the probe can deliver excitation light to a target site, which has optically accessible surface vessels that can serve as a flow channel, and collect the emitted fluorescence radiation. Some examples of suitable target sites can include, without limitation, the fingertip, sclera, wrist, oral mucosa or earlobe.

The Examples below provide further understanding of salient features of several embodiments of methods according to the teachings of the invention for performing flow cytometry. The Examples below are illustrative and are not intended to limit the scope of the invention disclosed herein.

Example 1

A multi-photon microscope was used to capture images of ex-vivo human lymphocytes and in-vivo mouse leukocytes to demonstrate the efficacy of the methods and systems according to the present invention for real-time imaging of cells. The multi-photon microscope used to image the cells was of the type shown schematically in FIG. 7. As illustrated, the two-photon imaging microscope includes a mode-locked Ti:sapphire laser (Spectra-Physics MaiTai-HP, wavelength 750 nm, 100 fs pulse width, 80 MHz repetition rate) pumping an optical parametric oscillator (Spectra-Physics OPAL), which in turn generates 100 fs pulses at a wavelength of 1180 nm. The 1180 nm laser pulses are focused into a β-barium borate crystal (BBO, CASIX USA, 2 mm thick) to generate 590 nm wavelength pulses with 60 mW of power.

The laser beam exiting the β-BBO crystal is deflected into a home-built video-rate (30 frames/second) x-y scanner 144. The scanner 144 includes a rotating polygon reflector 146 for directing the beam to two lens 148 and 150, which collimate the beam and direct to a galvanometer mirror 152 that can scan the beam to produce a two-dimensional scan. The beam exiting the scanner 144 is directed via mirrors 154, lenses 156, 158, and another mirror 160 to a dichroic beam splitter 162 (Semrock, FF510-Di01).

The beam passes through the dichroic beam splitter 162 and is then focused onto the sample by a 60×1.2 NA water-immersion microscope objective lens 164 (Olympus, UPlanAPO). The laser power at the sample site was 10 mW. The two-photon fluorescence signal from the sample in response to the incident laser pulses was epi-collected, deflected by the 510 nm long-pass dichroic mirror 162, and transmitted through a 330-380 nm band-pass filter 166 (Semrock, FF01-357/44). The fluorescent signal was then detected by a photomultiplier tube (PMT) 168 (Hamamatsu 3896) and the two-dimensional images in x-y plane were acquired by a frame grabber (Active Silicon, Snapper-8/24 PCI) installed on a Macintosh personal computer 170. Each image had 500×500 pixels. The imaging speed was 30 frames/sec and each static image was an average of 30 frames.

Figure 7:
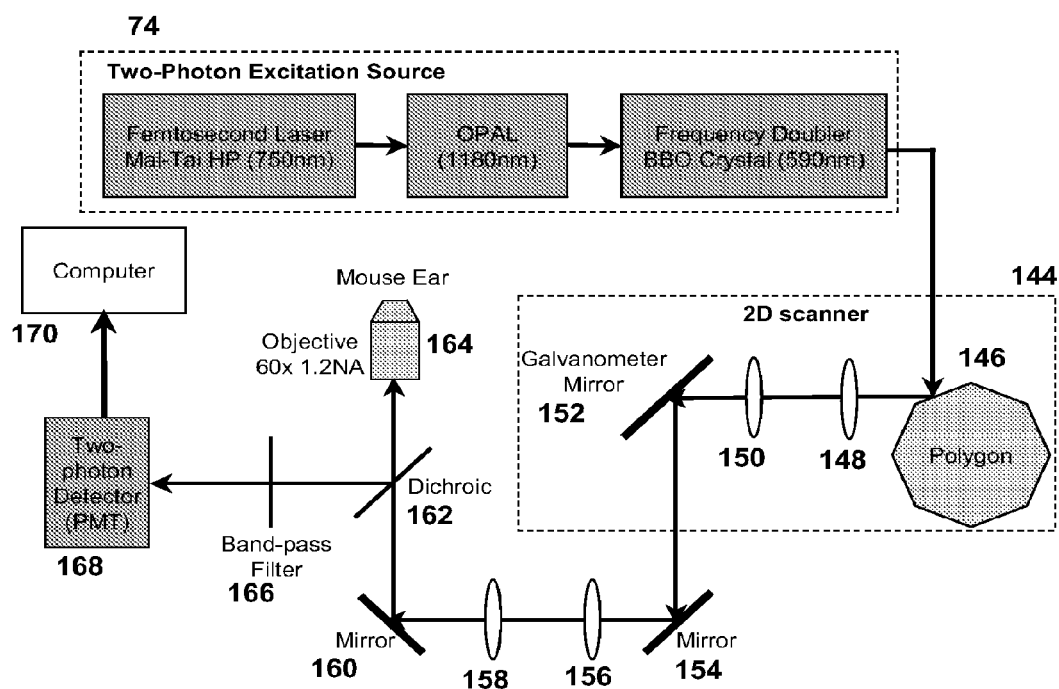
FIG. 7 schematically illustrates a two-photon microscope.
Figure 8A:
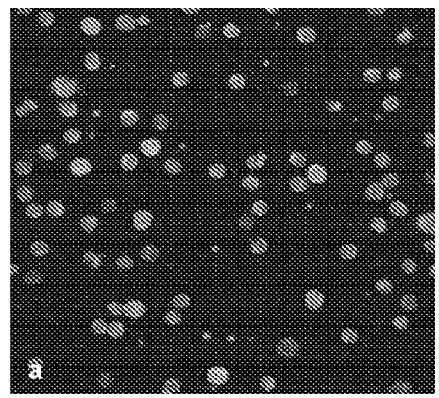
FIG. 8A is an two-photon microscope image of tryptophan fluorescence from ex vivo human lymphocytes in response to femtosecond excitation pulses obtained by utilizing the microscope of FIG. 7.

Using the system shown in FIG. 7, the cells were illuminated with laser light at a wavelength of 590 nm. Naturally occurring tryptophan within the cells was excited by the radiation via two-photon excitation, causing the tryptophan to fluoresce. FIG. 8A shows an image of the tryptophan fluorescence detected by the system from ex vivo human lymphocytes.

The system shown in FIG. 7 was also used to produce images of fluorescence emitted by in vivo mouse leukocytes in response to two-photon excitation by the laser pulses while flowing in the vasculature of an ear of a live mouse. In particular, FIG. 8B is an image of the tryptophan fluorescence detected by the system from in vivo leukocytes rolling in a blood vessel in the ear of a live mouse.

Figure 8B:
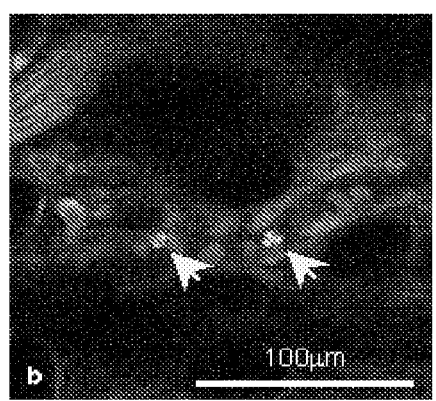
FIG. 8B is an two-photon microscope image of tryptophan fluorescence from an in vivo rolling mouse leukocyte in response to femtosecond excitation pulses obtained by utilizing the microscope of FIG. 7.

The results of these experiments, illustrated in FIGS. 8A and 8B, show that lymphocytes and leukocytes exhibit detectable tryptophan fluorescence in response to multi-photon excitation at 590 nm both ex vivo and in vivo.

Example 2

Figure 9A:
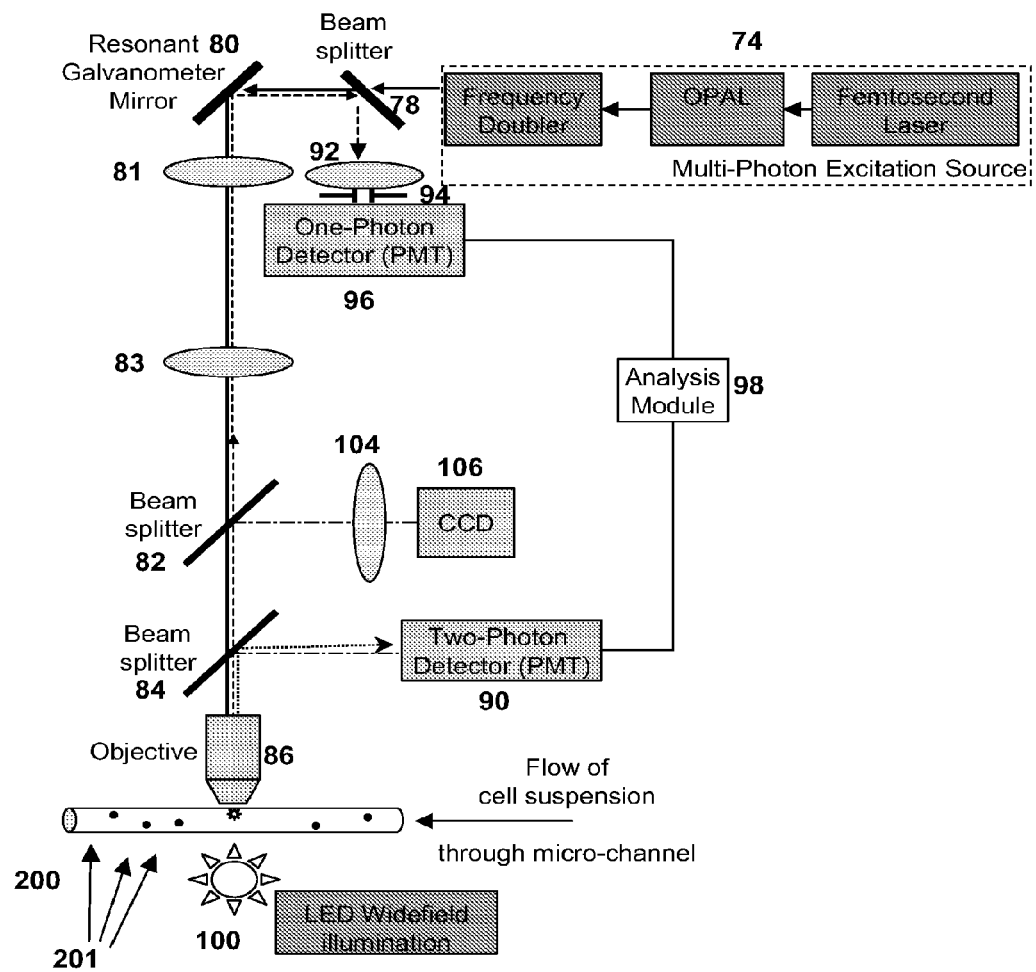
FIG. 9A schematically illustrates a system according to another embodiment of the invention for performing flow cytometry using one excitation source to excite both multi- and one-photon fluorescence.
Figure 9B:
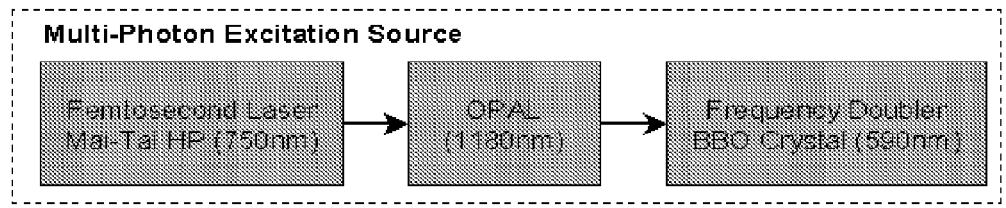
FIG. 9B schematically illustrates the various components of the excitation source of FIG. 9A.

A two-photon in vivo flow cytometer (TIFC) similar to the exemplary embodiment shown above in FIG. 5 was used to detect both two-photon tryptophan fluorescence and one-photon DiD fluorescence from stationary DiD-labeled cells. As shown in FIG. 9A, the experimental TIFC system setup was similar to the embodiment shown in FIG. 5 except that a single multi-photon excitation source 74 forms the radiation source. The source 74 was used to excite both two-photon fluorescence of endogenous tryptophan and one-photon fluorescence of exogenous DiD. The source generates laser light with a wavelength of 590 nm and pulse width of 100 fs using the elements schematically shown in FIG. 9B. The source generally includes a femtosecond laser, an optical parametric oscillator, and a frequency doubler. In this experiment, the laser was a mode-locked Ti:sapphire laser (Spectra-Physics MaiTai-HP) that generates ultra-short pulses (100 fs) at a wavelength of 750 nm. This light is then injected into an optical parametric oscillator (Spectra-Physics OPAL) to create a wavelength of 1180 nm, which is subsequently frequency doubled, by a β-barium borate crystal (BBO, CASIX USA, 2 mm thick), to create femtosecond pulses at 590 nm wavelength. The 590 nm pulsed-beam is generated with an average power of approximately 60 mW.

As shown in FIG. 9A, the pulsed beam generated by the multi-photon excitation source is transmitted through a dichroic beam splitter 78 (Chroma, Rockingham, Vt.) towards a resonant galvanometric mirror 80, which scans the beam in one direction at 8 kHz. A telecentric lens pair 81, 83 images the mirror surface onto the entrance pupil of the 60×1.2 NA focusing objective 86 (Olympus UPlanAPO). The combination of the objective 86 and galvanometric mirror 80 produce an "optical slit" across the blood vessel needed for cell counting. A large numerical aperture objective ensures a high photon density in the focus of the objective 86 for efficient generation of two-photon fluorescence.

A light emitting diode (LED) 100 at 527 nm back-illuminates the sample for widefield illumination. Light scattered through the sample is collected by the objective and reflected onto an imaging CCD 106 by a 560 nm long-pass dichroic beam splitter 82 (Chroma, Rockingham, Vt.). This enables visualization of the sample in order to position it within the optical slit for cell counting.

Two-photon generated tryptophan fluorescence collected by the objective 86 is reflected by a 510 nm long-pass dichroic beam splitter 84 (Semrock, Rochester, N.Y.) and detected by a photomultiplier tube detector 90 (PMT). One-photon generated DiD fluorescence collected by the objective 86 passes through the dichroic beam splitter 82, 84, travels back through the system to be de-scanned by the galvanometric mirror 80, and is reflected by a 630 nm short-pass dichroic beam splitter 78 (Chroma, Rockingham, Vt.). DiD fluorescence was then focused through a confocal pinhole 94 by lens 92 and was detected by a second PMT 96. Voltage levels from both PMTs were recorded for analysis by an analysis module 98.

Figure 10A:
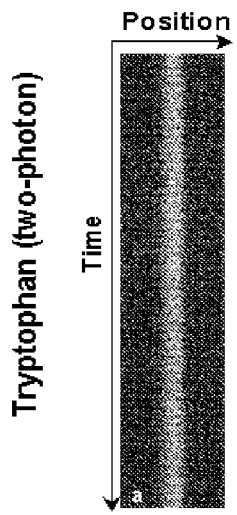
FIG. 10A is an image of the detected two-photon tryptophan fluorescence of a DiD-labeled stationary melanoma as detected by utilizing the system of FIG. 9A in response to two-photon excitation.
Figure 10B:
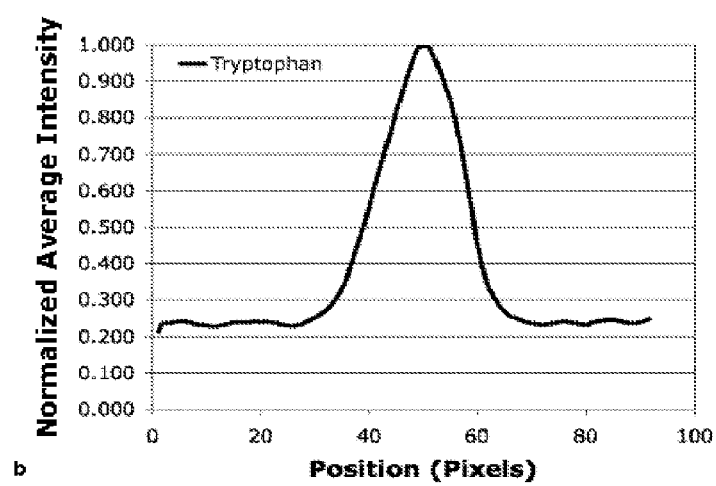
FIG. 10B is a plot of the normalized average intensity of the tryptophan fluorescence from each scan of the system of FIG. 9A across a DiD-labeled stationary melanoma cell as a function of position.
Figure 10C:
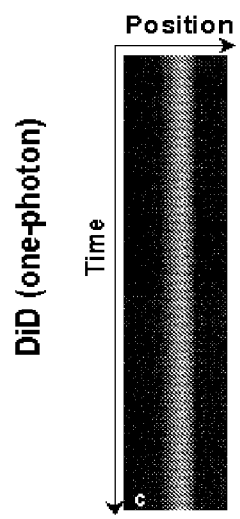
FIG. 10C is an image of the detected one-photon DiD fluorescence of a DiD-labeled stationary melanoma cell as detected by utilizing the system of FIG. 9A in response to two-photon excitation.
Figure 10D:
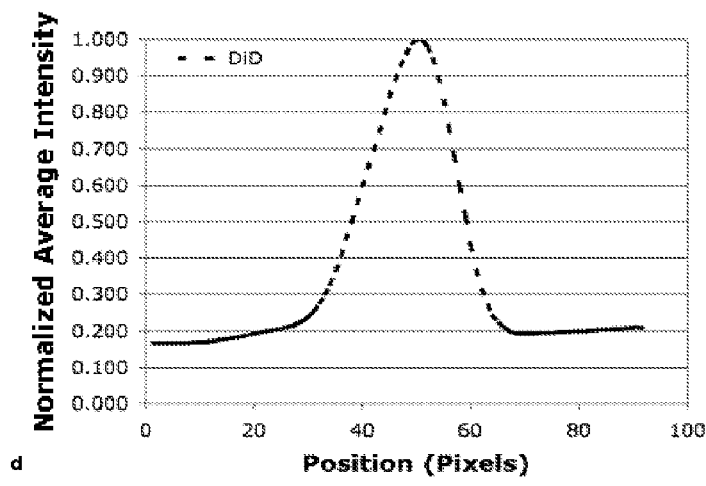
FIG. 10D is a plot of the normalized average intensity of the DiD fluorescence from each scan of the system in FIG. 9A across a DiD-labeled stationary melanoma cell as a function of position.

Using the TIFC system discussed above, a stationary (in vitro), DiD-labeled, melanoma cancer cell sitting stationary on a microscope slide in the focal plane of the TIFC was scanned with pulsed laser light at a wavelength of 590 nm. The data produced by this experiment is shown in FIGS. 10A-10D. FIGS. 10A and 10C are two separate channels from a single RGB frame and FIGS. 10B and 10D are the corresponding position traces. FIG. 10A shows the two-photon tryptophan fluorescence detected by the TIFC system. FIG. 10C shows the one-photon DiD fluorescence from the same cell detected by the TIFC system. Since the cell was stationary, the fluorescence remained constant over time and therefore appears as a vertical line in the image. The endogenous fluorophore tryptophan was detected at 335-379 nm in response to two-photon excitation. The exogenous DiD was detected simultaneously at 650-690 nm in response to one-photon excitation.

The plots of FIGS. 10B and 10D show the normalized average intensity of tryptophan fluorescence (FIG. 10B) and DiD fluorescence (FIG. 10D) from each scan of the TIFC system across the cell. These results show that the tryptophan and DiD fluorescence exhibited by a stationary in vitro DiD-labeled cell in the TIFC system focus are detectable by the system shown in FIG. 9A. The results of the scan and the plot of fluorescence intensity also show that the detected fluorescence signal can distinguish the location of a cell and be employed to measure the cell size. Additionally, the plots of tryptophan and DiD fluorescence shown in FIGS. 10B and 10D overlap in both time and position, demonstrating that the same cell was simultaneously detected by the system.

Figure 11A:
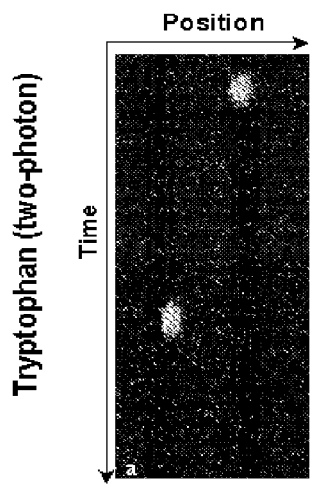
FIG. 11A is an image of the detected two-photon tryptophan fluorescence of DiD-labeled cells flowing through a micro-channel as detected by the two-photon excitation system shown in FIG. 9A.
Figure 11B:
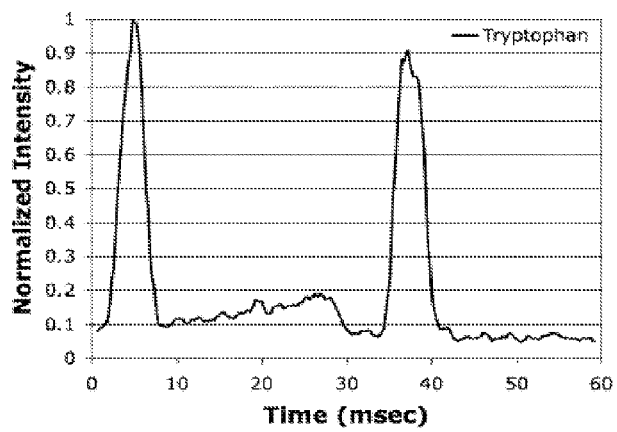
FIG. 11B is a plot of the normalized intensity of the tryptophan fluorescence of each cell in the scan of FIG. 11A as a function of time.
Figure 11C:
FIG. 11C is an image of the detected one-photon DiD fluorescence of DiD-labeled cells flowing through a micro-channel as detected by the two-photon excitation system shown in FIG. 9A.
Figure 11D:
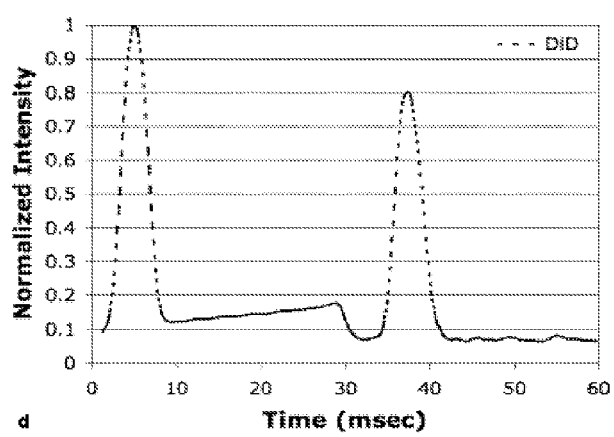
FIG. 11D is a plot of the normalized intensity of DiD fluorescence of each cell in the scan of FIG. 11A as a function of time.

The TIFC system discussed above was also used to scan DiD-labeled melanoma cells flowing through a micro-channel (150 μm in diameter) with pulsed laser light (100 fs pulses) at a wavelength of 590 nm. FIGS. 11A-11D show the data produced by this experiment. FIGS. 11A and 11C are two separate channels from a single RGB frame and FIGS. 11B and 11D are the corresponding time traces. FIG. 11A shows an image of the tryptophan fluorescence detected by 480 line-scans of the TIFC system (over 60 milliseconds), while FIG. 11C shows the detected DiD fluorescence from the same cells. The data shows two cells detected simultaneously in both channels. Since the cells are flowing through the "optical slit," their fluorescence is detected only for a short time. Consequently, the cells appear as individual objects rather than continuous vertical lines. As discussed above, both two-photon tryptophan fluorescence and one-photon DiD fluorescence were detected by the system. The plots of FIGS. 11B and 11D show the normalized intensity of the tryptophan fluorescence (FIG. 11B) and DiD fluorescence (FIG. 11D) from the cells as a function of time as they flow through the "optical slit" created by the scanner of the TIFC.

These results show that the tryptophan and DiD fluorescence exhibited by in vitro DiD-labeled cells flowing through a micro-channel in the focal plane of the TIFC is detectable by the system shown in FIG. 9A. Additionally, the plots of tryptophan and DiD fluorescence shown in FIGS. 11B and 11D overlap in both time and position, demonstrating that tryptophan and DiD fluorescence from each cell was simultaneously detected by the system.

Those having ordinary skill in the art will appreciate that various modifications can be made to the above embodiments without departing from the scope of the invention.

What is claimed is:

1. A method of performing in vivo flow cytometry, comprising illuminating at least a portion of blood circulating through a blood vessel in a live subject with radiation so as to excite at least one or more intrinsic cellular fluorophores of a plurality of circulating cells, and flow cytometrically detecting fluorescence radiation signal emitted by said one or more intrinsic cellular fluorophores in one or more of the circulating cells in response to said excitation.

2. The method of claim 1, further comprising analyzing said detected fluorescence radiation signal so as to obtain data about one or more circulating cell types of interest.

3. The method of claim 2, wherein the data comprises a relative concentration of the one or more circulating cell types of interest.

4. The method of claim 2, wherein the data indicates the presence of the one or more circulating cell types of interest.

5. The method of claim 1, wherein said illuminating step comprises selecting the illuminating radiation so as to cause multi-photon excitation of said one or more intrinsic cellular fluorophores.

6. The method of claim 5, wherein the illuminating step comprises applying at least one radiation pulse to the circulating blood.

7. The method of claim 6, wherein said radiation pulses have temporal durations less than about 1 nanosecond.

8. The method of claim 6, wherein said radiation pulses have temporal durations in a range of about 1 femtosecond to about 900 picoseconds.

9. The method of claim 1, wherein said intrinsic cellular fluorophores are selected from the group consisting of aromatic amino acids, the reduced form of nicotinamide adenine dinucleotide (NADH), flavin adenine dinucleotide (FAD), and porphyrins.

10. The method of claim 9, wherein the intrinsic cellular fluorophore is tryptophan.

11. The method of claim 9, wherein the intrinsic cellular fluorophore is protoporphyrin IX.

12. The method of claim 1, wherein said illuminating step comprises illuminating the circulating blood with a plurality of different excitation wavelengths for exciting different types of intrinsic cellular fluorophores at two or more different excitation wavelengths.

13. The method of claim 12, further comprising comparing intensity of detected fluorescence signals corresponding to excitation by said different wavelengths to distinguish fluorescence radiation emanating from different circulating cell types with intrinsic cellular fluorophores.

14. The method of claim 12, wherein one of said excitation wavelengths comprises about 295 nm and another of said excitation wavelengths comprises 255 nm.

15. The method of claim 1,
wherein the illuminating step comprises exciting the intrinsic cellular fluorophores of at least one circulating cell at a first interrogation site, and
further comprising the step of utilizing the detected fluorescence radiation signal to trigger interrogation of the at least one circulating cell at a second interrogation site.

16. The method of claim 15, wherein interrogation of the at least one circulating cell at a second interrogation site occurs after a predetermined time from the detecting step.

17. The method of claim 15, wherein interrogation of the at least one circulating cell at a second interrogation site comprises obtaining a scattering signature of the at least one cell.

18. The method of claim 15, wherein interrogation of the at least one circulating cell at a second interrogation site comprises obtaining an image of the at least one cell.

19. The method of claim 1, wherein the portion of blood is circulating through the blood vessel in a fingertip, sclera, wrist, oral mucosa, or earlobe of the live subject.

* * * * *